United States Patent [19]

Kemp

[11] 3,979,476

[45] *Sept. 7, 1976

[54] HYDROCARBON CONVERSION CATALYST AND PROCESS

[75] Inventor: Jacob D. Kemp, El Cerrito, Calif.

[73] Assignee: Chevron Research Company, San Francisco, Calif.

[ * ] Notice: The portion of the term of this patent subsequent to Dec. 3, 1991, has been disclaimed.

[22] Filed: Nov. 25, 1974

[21] Appl. No.: 526,668

Related U.S. Application Data

[63] Continuation of Ser. No. 324,924, Jan. 19, 1973, abandoned, which is a continuation-in-part of Ser. No. 268,296, July 3, 1972, abandoned.

[52] U.S. Cl................. 260/683.47; 260/683.51
[51] Int. Cl.$^2$............................................ C07C 3/54
[58] Field of Search................ 260/683.47, 683.58, 260/683.53, 683.51

[56] References Cited

UNITED STATES PATENTS

| | | | |
|---|---|---|---|
| 3,678,120 | 7/1972 | Bloch | 260/683.47 |
| 3,852,371 | 12/1974 | Kemp | 260/683.47 |

*Primary Examiner*—G. J. Crasanakis
*Attorney, Agent, or Firm*—G. F. Magdeburger; R. H. Davies; J. D. Foster

[57] ABSTRACT

A catalytic composite suitable for hydrocarbon conversion processes, comprising hydrogen fluoride-antimony pentafluoride supported on fluorided alumina, having a fluorine content of at least 55 weight percent. Preferably the fluorided alumina support contains at least 60 weight percent fluorine and has a surface area less than 10 m$^2$/gram. The catalyst is particularly useful for isomerization and alkylation processes.

3 Claims, No Drawings

HYDROCARBON CONVERSION CATALYST AND PROCESS

CROSS-REFERENCE TO RELATED APPLICATION

This application is a continuation of my copending application Ser. No. 324,924, filed Jan. 19, 1973, now abandoned, which is, in turn, a continuation-in-part of my copending application Ser. No. 268,296, filed July 3, 1972, and now abandoned.

BACKGROUND OF THE INVENTION

The present invention relates to a catalyst composition suitable for hydrocarbon conversion processes such as isomerization, alkylation and polymerization. More particularly, the present invention relates to a catalyst composition comprising hydrogen fluoride-antimony pentafluoride on an alumina support, and the use of the catalyst in processes such as isomerization.

Isomerization of normal paraffins such as n-pentane, n-hexane or n-heptane is widely practiced for production of higher-octane isomers for use in gasoline.

Table I, below, shows the incentive for isomerization.

TABLE I

| Hydrocarbon | Research Octane | | Motor Octane | |
|---|---|---|---|---|
| | Clear | 3 cc. TEL | Clear | 3 cc. TEL |
| n-Pentane | 62 | 89 | 62 | 84 |
| i-Pentane | 92 | 109 | 90 | 105 |
| n-Hexane | 25 | 65 | 26 | 65 |
| 2-methylpentane | 73 | 93 | 74 | 91 |
| 3-methylpentane | 75 | 93 | 74 | 91 |
| 2,2-Dimethylbutane (neohexane) | 92 | 106 | 93 | 113 |
| 2,3-Dimethylbutane (diisopropyl) | 103 | 119 | 94 | 112 |

Isomerization processes can be divided into high, low, and ultra-low temperature processes. Rough temperature ranges are: 500°–800°F. for high-temperature isomerization; 150°–400°F. for low-temperature isomerization; and −50°F. to 150°F. for ultra-low-temperature isomerization. In the past, commercial operation has been mostly low-temperature isomerization utilizing a catalyst containing $AlCl_3$.

For typical low-temperature isomerization, the catalyst used is $AlCl_3$ plus hydrogen chloride. Low-temperature isomerization feedstock, dried and preheated to reaction temperature, is combined with a recycle stream (if recycling is practiced), mixed with hydrogen chloride, and passed through a reactor and an aluminum chloride recovery section. Reactor effluent is cooled and flashed to discharge any light gases through a small absorber that recovers hydrogen chloride carried off in the gases. Liquid from the flash drum is stripped to recover hydrogen chloride, and is caustic-washed to remove the last traces of acid. The stripping column is usually operated at a pressure high enough that the stripped hydrogen chloride can be returned directly to the reactor. If recycling of unconverted normal paraffin is practiced, the recycle stream is then fractionated from the product.

Typical reaction conditions are:
| | |
|---|---|
| Catalyst | $AlCl_3$—HCl |
| Inhibitor | $H_2$(60 psi) |
| Pressure, psi | 300 |
| Temperature, °F. | 176 – 212 |
| Space Velocity, V/hr/V | 1.0 – 2.5 |
| HCl Conc., Wt.% | 5 |
| Conversion % | 60 |

Ultra-low temperature isomerization so far has not been commercially employed. However, there is considerable incentive to develop a commercially attractive low-temperature isomerization process, because the lower the temperature the more favorable is the equilibrium for isoparaffin relative to normal paraffins. Ultra-low temperatures are especially attractive for substantial production of the very high-octane dimethylbutanes.

U.S. Pat. No. 2,956,095 describes an ultra-low-temperature isomerization process employing a fluorosulfonic-acid catalyst instead of a Friedel-Crafts type catalyst such as $AlCl_3$.

U.S. Pat. No. 3,201,494 and U.S. Pat. No. 3,394,202 are also directed to ultra-low-temperature isomerization and are especially pertinent to the present invention.

U.S. Pat. No. 3,201,494 is directed to liquid-phase isomerization of hydrocarbons using a hexafluoro-antimonic acid catalyst in hydrofluoric acid, which catalyst is obtained, according to Example 1 of the patent, by dissolving antimony pentafluoride in hydrofluoric acid.

U.S. Pat. No. 3,394,202 is also directed to isomerization using a hydrogen fluoride-antimony pentafluoride acid catalyst, but is the U.S. Pat. No. 3,394,202 the catalyst is supported on an inert support such as fluorided alumina. According to U.S. Pat. No. 3,394,202:

"...suitable inert carriers may be prepared from solids which are not inert but which have been treated to make them inert, e.g., coated with a thin layer of inert material. This embodiment of the invention may be preferred in many cases, since it is usually desirable to support the acid on a carrier having a high surface area for maximum contact area with hydrocarbons to be converted. ...An example of material having a high surface area which may be treated to provide supports of the invention are alumina, silica, ... Although the specific surface area of the porous carrier is slightly decreased as a result of the treatment, inert carriers with a specific surface area of at least 100 m²/gm. are easily prepared. Desirable surface areas are from 10 to about 500 m²/gm., preferably 20 to 200 m²/gm., with pore diameters greater than 10 A, and preferably 100–1000 A."

Quite similar to U.S. Pat. No. 3,394,202, U.S. Pat. No. 3,678,120 is directed to a catalyst composition comprising HF-antimony pentafluoride on an inert support, such as charcoal. According to U.S. Pat. No. 3,678,120, the inert support should have:

"...a surface area of about 50 square meters per gram to about 1000 square meters per gram or more, and which, when combined with the active catalytic complex will not substantially lower the catalytic activity of the combined complex, nor will the complex destroy the structural integrity and surface area of the solid support."

My U.S. Pat. No. 3,852,371 discloses an alkylation process using a fluorided alumina catalyst, in which a portion of the effluent from the reaction zone is recycled thereto.

SUMMARY

According to the present invention, a catalytic composite is provided which is suitable for hydrocarbon conversion processes comprising hydrogen fluoride-antimony pentafluoride supported on fluorided alumina having a fluorine content of at least 55 weight percent.

Preferably the more highly fluorided alumina support, which forms a critical part of the catalyst of the present invention, contains at least 60 weight percent fluorine. The fluorine is calculated as the monoatomic element F.

It is especially preferred that the surface area of the highly fluorided support be less than 10 m$^2$/gm.

Among other factors, the present invention is based on the finding that a superior hydrocarbon conversion catalyst can be obtained, in particular a catalyst with a lower deactivation rate, by highly fluoriding the alumina support of the present catalyst before HF-antimony pentafluoride is added to the catalyst.

The maximum theoretical amount of fluorine which can be put into an alumina support is about 67.8 weight percent fluorine, calculated as F. This maximum theoretical possible fluorine assumes that all of the $Al_2O_3$ is converted to $AlF_3$. Putting only a thin layer of fluorine on the surface would probably result in only about 10–30 weight percent fluorine for the fluorided alumina. In contrast to this, the most preferred catalyst of the present invention is a fluorided alumina support having at least 62 weight percent fluorine.

Also, in the area of catalysis, one normally expects that it is most desirable to have a relatively high surface area. However, I have found that the better hydrocarbon conversion catalyst system for HF-antimony pentafluoride on fluorided alumina is achieved by using a relatively low surface area fluorided alumina support, namely a surface area less than 10 m$^2$/gm. For example, preferred surface areas for the catalyst of the present invention are between 0.1 and 10 m$^2$/gm., more preferably between 1 and 5 m$^2$/gm. The low surface area is believed to result from the high degree of fluoriding required for the fluorided alumina support for the catalyst of the present invention.

Although the surface area of the catalyst is especially preferred to be below 10 m$^2$/gm., it is nonetheless strongly preferred that the fluorided alumina support be porous, having a pore volume between 0.05 and 0.07 cc per gram of support, more preferably between 0.1 and 0.5 cc's per gram of support, and still more preferably between 0.3 and 0.5 cc's per gram of support.

The alumina support for the catalyst can be fluorided in gas phase by contacting the alumina with anhydrous hydrogen fluoride. Alternately, it has been found that a preferred means of fluoriding alumina support is by contacting the alumina with liquid anhydrous hydrogen fluoride under a blanket of liquid pentane.

According to a preferred embodiment of the present invention, a hydrocarbon conversion process is provided which comprises contacting a hydrocarbon, at hydrocarbon conversion conditions, with a catalytic composite comprising hydrogen fluoride-antimony pentafluoride supported on fluorided alumina having a fluorine content of at least 60 weight percent.

Hydrocarbon isomerization is advantageously carried out with the catalyst of the present invention. Preferably, the isomerization is carried out at a temperature between −80° and 150°F. and under sufficient pressure to maintain the reactants in liquid phase. The feedstock can be chosen from various isomerizable hydrocarbons, but paraffinic hydrocarbons are preferred feedstocks. Paraffins such as $C_4$-$C_9$ normal paraffins, or mildly branched $C_4$-$C_9$ isoparaffins are particularly preferred feedstocks.

The catalyst of the present invention is particularly advantageously used to react an olefin with an alkylatable hydrocarbon, such as an isoparaffin, under alkylation conditions. Preferred alkylation conditions include a temperature of about −30° to 150°F. and a pressure sufficient to maintain the reactants in liquid phase. Preferred alkylatable hydrocarbon feedstocks are $C_4$-$C_6$ isoparaffins and preferred olefins are $C_2$-$C_6$ olefins with $C_3$ and $C_4$ olefins being particularly preferred.

The catalyst of the present invention can also be used for polymerizing polymerizable hydrocarbons as, for example, polymerizing olefins. Using the catalyst of the present invention, low temperatures are also preferred for the polymerizing of hydrocarbons, namely, temperatures between about −80° and 150°F.

EXAMPLE

Two supported HF-antimony pentafluoride catalysts were prepared, namely, Catalyst A supported on a fluorided alumina having 53.8 weight percent fluorine and Catalyst B supported on a fluorided alumina having 62 weight percent fluorine. The base for Catalyst A was prepared by four successive stages of fluoriding the alumina with liquid anhydrous HF. The alumina was stirred under normal pentane while slowly adding liquid anhydrous HF in excess. The normal pentane kept the temperature low while the reaction of the alumina and HF proceeded. The normal pentane and excess liquid HF were decanted. Absorbed water, HF and normal pentane were removed from the fluorided alumina by successively sweeping with nitrogen at room temperature, then under a vacuum of 21 inches mercury at 210°F., followed by calcination in a muffle furnace with an air purge. In stages 1 and 2, the calcination was done for 2 hours at 900°F. In stages 3 and 4, the calcination was performed at 1250°F. for 2 hours. The procedure for the base of Catalyst B was similar to that for the base of Catalyst A, except that there were only three successive stages of fluoridation.

Catalysts A and B were tested for the alkylation of olefins by isobutane. Specifically, a fresh feed consisting of isobutane and butene-2 was fed continuously to a 0.18 inch i.d. jacketed tubular steel reactor containing a 14 inch fixed bed of the catalyst being tested, at a pressure sufficient to maintain liquid-phase operation. Reaction mix hydrocarbon was recycled from the reactor outlet to the reactor inlet to mix with and dilute the incoming fresh feed. The reaction mix was analyzed chromatographically. Operation conditions and olefin utilization are summized below in Table II.

TABLE II

| | Catalyst A (Run 125-168) | | Catalyst B (Run 125-170) | |
| --- | --- | --- | --- | --- |
| Temperature, °F. | 50 | | 51 | |
| Isobutane in reaction mixture, vol.% | 89 | | 65 | |
| Volume of catalyst, C.C. | 6 | | 6 | |
| Butene-2 in feed, vol.% | 5.0 | | 4.4 | |
| | | Hours | | Hours |
| Vol. recycle/vol. feed | 17 | First 50 | 62.5 | First 70 |
| | 45–100 | 50–160 | 80 | 70–140 |
| | | | 25 | 140–210 |
| Vol. feed/vol. catalyst | | | | |

TABLE II-continued

| per hour | 6.67 | First 50 | 6.67 | First 70 |
|---|---|---|---|---|
| | 3.33 | 50–120 | 3.33 | 70–140 |
| | 1.67 | 120–140 | 6.67 | 140–210 |
| | 0.83 | 140–160 | | |
| Vol. Butene-2/vol. catalyst/hour | 0.32 | First 50 | 0.29 | First 70 |
| | 0.17 | 50–120 | 0.15 | 70–140 |
| | 0.095 | 120–140 | 0.31 | 140–210 |
| | 0.042 | 140–160 | | |
| Olefin utilization (% butene alkylated) | 100 | 1st 58 | 100 | 0–210 |
| | 94 | at 94 | | |
| | 96.6 | at 131 | | |
| | 90.3 | at 140 | | |
| | 96.2 | at 162 | | |

Tables III and IV below contain data from the runs with Catalysts A and B, but in more detail than in Table II. "RM" in Tables III and IV stands for "reaction mixture" at the outlet of the reaction zone.

As can be seen from the olefin utilization at the bottom of summary Table II, the alkylation run with Catalyst A had olefin breakthrough after 100 hours of operation, so that the olefin utilization dropped below 100%. In alkylation processes, it is especially desirable to have 100% olefin utilization in order to avoid polymerization of the olefins to undesired heavy polymers which, among other things, can contribute to high catalyst consumption.

After the olefin utilization dropped below 100% in the run with Catalyst A, the volume of olefin feed to the reaction zone was decreased to try to prevent the olefin utilization from rapidly dropping off further. It can be noted that in the alkylation run with Catalyst B, the catalyst supported on the highly fluorided alumina, the olefin utilization stayed at 100% throughout the duration of the 210-hour alkylation run. Subsequent alkylation runs have confirmed the high stability and activity for the catalyst supported on a highly fluorided alumina; also, isomerization runs have confirmed the superiority of the catalyst supported on the highly fluorided alumina.

The alkylate octane numbers are a function of the catalyst activity, isobutane concentration and total feed space rate at any given temperature. The lower-octane-number product obtained with Catalyst B compared to the product of Catalyst A at comparable total feed space rates is the result of the higher activity of Catalyst B, which increases the extent of product isomerization, producing lower-octane-number molecules. However, the higher activity of Catalyst B allows a higher feed throughput at nearly complete olefin utilization, resulting in increased plant capacity, decreased isomerization and increased octane number over that with the less active Catalyst A.

TABLE III

Run 125-168

| Catalyst | | |
|---|---|---|
| Treated alumina base: B-682-10, | 66.7 wt.% of catalyst, 53.8 wt.% F (calc. as F), 3 m²/g. surface area | |
| Liquid acid phase (HF . SbF₅) | 33.3 wt.% of catalyst (73.2 wt.% SbF₅, 26.8 wt.% HF) | |

| Period | (1) | (2) | (3) |
|---|---|---|---|
| Temperature, °F. | 50 | 50 | 50 |
| Vol.% olefin in feed | 4.17 | 5.32 | 5.08 |
| Wt.% isobutane in RM (calc.) | 90 | 88 | 89 |
| Vol. feed/Vol. cat./hr. | 6.67 | 6.67 | 3.33 |
| Vol. olefin/Vol. cat./hr. | 0.28 | 0.35 | 0.17 |
| Vol. RM recycle/Vol. feed | 17 | 17 | 45 |

| Hours operation | 0–23.5 | 8.4 | 20.4 | 23.5–47 | 28.9 | 47 | 52.6–123.2 | 58.6 | 122.3 |
|---|---|---|---|---|---|---|---|---|---|
| Analysis (wt.%) | Feed | C₅+Prod. | C₅+Prod. | Feed | C₅+Prod. | C₅+Prod. | Feed | C₅+Prod. | C₅+Prod. |
| Isobutane | 94.48 | — | — | 94.12 | — | — | 94.49 | — | — |
| n-Butane | — | — | — | — | — | — | — | — | — |
| Butene-2 | 4.51 | — | — | 5.76 | — | — | 5.51 | — | — |
| Isopentane | — | 2.36 | 2.16 | — | 2.15 | 2.29 | — | 2.78 | 3.53 |
| n-Pentane | — | 0.03 | 0.03 | — | 0.03 | 0.07 | — | 0.11 | 0.04 |
| 2,2-DMB | — | 0.07 | 0.06 | — | 0.06 | 0.12 | — | 0.17 | 0.08 |
| 2,3-DMB | — | 0.75 | 0.66 | — | 0.70 | 0.67 | — | 0.59 | 1.58 |
| 2-MP | — | 0.33 | 0.25 | — | 0.21 | 0.26 | — | 0.34 | 0.34 |
| 3-MP | — | 0.13 | 0.10 | — | 0.09 | 0.12 | — | 0.15 | 0.34 |
| n-Hexane | — | — | — | — | — | 0.01 | — | 0.01 | 0.01 |
| 2,4-DMP | — | 1.07 | 0.90 | — | 0.92 | 0.89 | — | 0.81 | 1.18 |
| 2,2,3-TMD | — | — | — | — | — | 0.02 | — | 0.02 | 0.12 |
| 2,3-DMP | — | 0.60 | 0.50 | — | 0.49 | 0.53 | — | 0.55 | 1.33 |
| 3-MHx | — | 0.08 | 0.08 | — | 0.04 | 0.05 | — | 0.09 | 0.06 |
| 2,2,4-TMP | — | 46.64 | 48.05 | — | 47.64 | 47.29 | — | 47.99 | 32.91 |
| 2,5+2,4+2,2-DMHx | — | 9.86 | 7.67 | — | 6.93 | 6.45 | — | 6.86 | 4.51 |
| 2,3,4-TMP | — | 17.22 | 18.55 | — | 20.08 | 19.88 | — | 18.51 | 17.35 |
| 2,3,3-TMP | — | 11.89 | 11.67 | — | 11.52 | 10.83 | — | 10.18 | 7.59 |
| 2-MHp | — | 3.21 | 3.07 | — | 3.14 | 3.09 | — | 3.06 | 2.60 |
| 4-MHp+3,4-DMHx | — | 1.27 | 0.90 | — | 0.91 | 0.81 | — | 0.95 | 0.20 |
| 3-MHp | — | 0.41 | 0.27 | — | 0.23 | 0.20 | — | 0.28 | 0.24 |
| 2,2,5-TMHx | — | 0.77 | 0.82 | — | 0.85 | 0.92 | — | 0.83 | 2.71 |
| Nonane+ | — | 2.81 | 3.29 | — | 3.93 | 5.49 | — | 5.77 | 23.66 |
| Mol. isobutane consumed/Mol. butene | — | 1.02 | 0.99 | — | 1.01 | 1.00 | — | 1.02 | 0.93 |
| % butene alkylated* | — | 100 | 100 | — | 100 | 100 | — | 100 | 94 |
| F-1 Octane No. | — | 92.8 | 93.0 | — | 94.0 | 93.9 | — | 93.5 | 91.4 |

| Period | | (4) | | (5) |
|---|---|---|---|---|
| Temperature, °F. | | 50 | | 50 |
| Vol.% olefin in feed | | 5.08 | | 5.08 |
| Wt.% isobutane in RM (calc.) | | 89 | | 89 |
| Vol. feed/Vol. cat./hr. | | 1.67 | | 0.83 |
| Vol. olefin/Vol. cat./hr. | | 0.095 | | 0.042 |
| Vol. RM recycle/Vol. feed | | 60 | | 100 |

| Hours operation | 123.2–165.4 | 131.3 | 140.3 | 149.5 | 161.5 |
|---|---|---|---|---|---|

TABLE III-continued

Run 125-168

| Catalyst | | | | | |
|---|---|---|---|---|---|
| Treated alumina base: B-682-10, | 66.7 wt.% of catalyst, 53.8 wt.% F (calc. as F), 3 m²/g. surface area | | | | |
| Liquid acid phase (HF . SbF₅) | 33.3 wt.% of catalyst (73.2 wt.% SbF₅, 26.8 wt.% HF) | | | | |

| Analysis (wt.%) | Feed | C₅+Prod. | C₅+Prod. | C₅+Prod. | C₅+Prod. |
|---|---|---|---|---|---|
| Isobutane | 94.49 | — | — | — | — |
| n-Butane | — | — | — | — | — |
| Butene-2 | 5.51 | — | — | — | — |
| Isopentane | — | 3.98 | 3.90 | 4.01 | 3.98 |
| n-Pentane | — | 0.02 | 0.01 | 0.01 | 0.01 |
| 2,2-DMB | — | 0.05 | 0.04 | 0.05 | 0.02 |
| 2,3-DMB | — | 2.14 | 2.13 | 2.30 | 2.24 |
| 2-MP | — | 0.46 | 0.43 | 0.47 | 0.44 |
| 3-MP | — | 0.41 | 0.46 | 0.45 | 0.44 |
| n-Hexane | — | — | — | — | — |
| 2,4-DMP | — | 1.52 | 1.37 | 1.56 | 1.51 |
| 2,2,3-TMB | — | 0.15 | 0.02 | 0.03 | — |
| 2,3-DMP | — | 1.67 | 1.78 | 1.87 | 1.76 |
| 3-MHx | — | 0.06 | 0.06 | 0.07 | 0.03 |
| 2,2,4-TMP | — | 29.52 | 28.11 | 28.47 | 29.66 |
| 2,5+2,4+2,2-DMHx | — | 5.55 | 5.20 | 5.88 | 5.74 |
| 2,3,4-TMP | — | 17.10 | 17.16 | 17.62 | 18.22 |
| 2,3,3-TMP | — | 7.31 | 7.35 | 7.41 | 7.55 |
| 2-MHp | — | 3.21 | 3.40 | 3.58 | 3.71 |
| 4-MHp+3,4-DMHx | — | 0.17 | 0.18 | 0.21 | 0.17 |
| 3-MHp | — | 0.33 | 0.53 | 0.41 | 0.43 |
| 2,2,5-TMHx | — | 3.38 | 3.39 | 3.67 | 3.22 |
| Nonane+ | — | 23.08 | 24.47 | 21.96 | 20.86 |
| Mol. isobutane consumed/Mol. butene | — | 0.95 | 0.97 | 0.935 | 0.936 |
| % butene alkylated* | — | 96.6 | 90.3 | 96.9 | 96.2 |
| F-1 Octane No. | — | 90.2 | 89.7 | 89.8 | 90.0 |

*estimated

TABLE IV

Run 125-170

| Catalyst | | |
|---|---|---|
| Treated alumina base: B-682-22, | 65.0 wt.% of catalyst, (62.0 wt.% F, <10m²/g. surface area | |
| Liquid acid phase | 35.0 wt.% of catalyst (73.9 wt.% SbF₅, 26.1 wt.% HF) | |

| Period | (1a) | (1b) | (1c) |
|---|---|---|---|
| Temperature, °F. | 51 | 51 | 51 |
| Vol.% olefin in feed | 4.36 | 4.35 | 4.36 |
| Wt.% isobutane in RM (calc.) | 64.5 | 66.4 | 64.3 |
| Vol. feed/Vol. cat./hr. | 6.67 | 6.67 | 6.67 |
| Vol. olefin/Vol. cat./hr. | 0.29 | 0.29 | 0.29 |
| Vol. RM recycle/Vol. feed | 62.5 | 57.5 | 52.5 |

| Hours operation | 0–21.5 | 9.3 | 21.4 | 21.5–44.5 | 33.4 | 42.6 | 44.5–70.3 | 48.6 | 70.0 |
|---|---|---|---|---|---|---|---|---|---|
| Analysis (wt.%) | Feed | C₅+Prod. | C₅+Prod. | Feed | C₅+Prod. | C₅+Prod. | Feed | C₅+Prod. | C₅+Prod. |
| Isobutane | 70.09 | — | — | 72.00 | — | — | 70.09 | — | — |
| n-Butane | 25.21 | — | — | 23.30 | — | — | 25.21 | — | — |
| Butene-2 | 4.68 | — | — | 4.68 | — | — | 4.68 | — | — |
| Isopentane | — | 9.72 | 12.38 | — | 13.14 | 13.25 | — | 13.10 | 12.13 |
| n-Pentane | — | 0.29 | 0.50 | — | 0.54 | 0.46 | — | 0.49 | 0.37 |
| 2,2-DMB | — | 0.40 | 0.62 | — | 0.69 | 0.62 | — | 0.66 | 0.55 |
| 2,3-DMB | — | 1.29 | 1.40 | — | 1.48 | 1.47 | — | 1.65 | 1.58 |
| 2-MP | — | 1.53 | 1.90 | — | 2.12 | 1.99 | — | 2.20 | 2.00 |
| 3-MP | — | 0.64 | 0.79 | — | 0.88 | 0.83 | — | 0.92 | 0.83 |
| n-Hexane | — | 0.05 | 0.08 | — | 0.09 | 0.08 | — | 0.10 | 0.07 |
| 2,4-DMP+2,2-DMP | — | 1.81 | 1.84 | — | 1.95 | 1.91 | — | 2.19 | 2.12 |
| 2,2,3-TMB | — | 0.14 | 0.18 | — | 0.20 | 0.17 | — | 0.21 | 0.18 |
| 2,3-DMP+3,3-DMP | — | 1.76 | 2.00 | — | 2.18 | 2.08 | — | 2.29 | 2.19 |
| 3-MHx | — | 0.55 | 0.67 | — | 0.75 | 0.69 | — | 0.76 | 0.72 |
| 2,2,4-TMP | — | 34.20 | 30.06 | — | 28.30 | 29.02 | — | 28.70 | 29.52 |
| 2,5+2,4+2,2-DMHx | — | 16.35 | 15.83 | — | 16.88 | 16.51 | — | 16.63 | 17.45 |
| 2,3,4-TMP | — | 9.56 | 9.53 | — | 8.39 | 8.58 | — | 8.22 | 7.90 |
| 2,3,3-TMP | — | 8.26 | 7.29 | — | 6.74 | 7.00 | — | 6.74 | 7.01 |
| 2-MHp | — | 3.12 | 3.03 | — | 2.98 | 2.91 | — | 2.83 | 2.82 |
| 4-MHp+3,4-DMHx | — | 3.36 | 3.75 | — | 4.22 | 3.94 | — | 3.84 | 3.81 |
| 3-MHp | — | 1.61 | 1.88 | — | 2.15 | 1.98 | — | 1.93 | 1.86 |
| 2,2,5-TMHx | — | 2.19 | 2.51 | — | 2.75 | 2.76 | — | 2.73 | 2.92 |
| Nonane+ | — | 3.16 | 3.74 | — | 3.57 | 3.79 | — | 3.90 | 4.68 |
| Mol. isobutane consumed/Mol. butene | — | 1.15 | 1.14 | — | 1.15 | 1.15 | — | 1.21 | 1.19 |
| % butene alkylated* | — | 100 | 100 | — | 100 | 100 | — | 100 | 100 |
| F-1 Octane No. | — | 85.1 | 84.1 | — | 82.9 | 83.8 | — | 83.1 | 84.1 |

| Period | (2) | (3a) | (3b) |
|---|---|---|---|
| Temperature, °F. | 51 | 51 | 51 |
| Vol. % olefin in feed | 4.55 | 4.74 | 4.49 |
| Wt. % isobutane in RM (calc.) | 64.5 | 66 | 67 |
| Vol. feed/Vol. cat./hr. | 3.33 | 6.67 | 6.67 |
| Vol. olefin/Vol. cat./hr. | 0.15 | 0.32 | 0.30 |
| Vol. RM recycle/Vol. feed | 80 | 25 | 25 |

| Hours operation | 70.3–138.9 | 76 | 137.2 | 141.5–168 | 143.2 | 163.4 | 168–231.8 | 172.4 | 230.0 |
|---|---|---|---|---|---|---|---|---|---|

TABLE IV-continued

Run 125-170

| Catalyst | | | | | | | | |
|---|---|---|---|---|---|---|---|---|
| Treated alumina base: B-682-22, | | | 65.0 wt.% of catalyst, (62.0 wt.% F, <10m²/g. surface area | | | | | |
| Liquid acid phase | | | 35.0 wt.% of catalyst (73.9 wt.% SbF₅, 26.1 wt.% HF) | | | | | |

| Analysis (wt.%) | Feed | C₅+Prod. | C₅+Prod. | Feed | C₅+Prod. | C₅+Prod. | Feed | C₅+Prod. | C₅+Prod. |
|---|---|---|---|---|---|---|---|---|---|
| Isobutane | 71.01 | — | — | 71.94 | — | — | 72.16 | — | — |
| n-Butane | 24.02 | — | — | 22.87 | — | — | 23.00 | — | — |
| Butene-2 | 4.89 | — | — | 5.10 | — | — | 4.83 | — | — |
| Isopentane | — | 16.82 | 17.78 | — | 12.35 | 7.49 | — | 7.65 | 6.06 |
| n-Pentane | — | 0.70 | 0.53 | — | 0.24 | 0.07 | — | 0.07 | 0.07 |
| 2,2-DMB | — | 0.93 | 0.73 | — | 0.36 | 0.13 | — | 0.12 | 0.11 |
| 2,3-DMB | — | 1.61 | 1.63 | — | 1.70 | 1.44 | — | 1.32 | 1.21 |
| 2-MP | — | 2.88 | 3.07 | — | 2.19 | 1.22 | — | 1.21 | 0.96 |
| 3-MP | — | 1.21 | 1.28 | — | 0.90 | 0.50 | — | 0.49 | 0.39 |
| n-Hexane | — | 0.14 | 0.10 | — | 0.04 | 0.01 | — | 0.01 | — |
| 2,4-DMP+2,2-DMP | — | 2.12 | 2.10 | — | 2.24 | 2.04 | — | 1.88 | 1.64 |
| 2,2,3-TMB | — | 0.23 | 0.18 | — | 0.15 | 0.11 | — | 0.10 | 0.09 |
| 2,3-DMP+3,3-DMP | — | 2.81 | 2.88 | — | 2.29 | 1.65 | — | 1.55 | 1.24 |
| 3-MHx | — | 1.08 | 1.11 | — | 0.74 | 0.43 | — | 0.41 | 0.31 |
| 2,2,4-TMP | — | 21.66 | 17.22 | — | 26.28 | 34.38 | — | 34.84 | 41.32 |
| 2,5+2,4+2,2-DMHx | — | 20.67 | 24.32 | — | 21.34 | 20.66 | — | 21.09 | 15.43 |
| 2,3,4-TMP | — | 4.56 | 2.90 | — | 5.24 | 6.73 | — | 6.69 | 9.93 |
| 2,3,3-TMP | — | 5.37 | 4.41 | — | 6.67 | 9.02 | — | 9.09 | 10.19 |
| 2-MHp | — | 2.75 | 2.86 | — | 2.87 | 3.05 | — | 3.16 | 2.92 |
| 4-MHp +3,4-DMHx | — | 5.23 | 5.88 | — | 3.91 | 2.76 | — | 2.89 | 2.07 |
| 3-MHp | — | 2.72 | 3.02 | — | 1.89 | 1.16 | — | 1.24 | 0.86 |
| 2,2,3-TMHx | — | 3.10 | 3.71 | — | 3.65 | 2.82 | — | 2.52 | 2.00 |
| Nonane+ | — | 3.67 | 4.27 | — | 5.00 | 3.35 | — | 3.70 | 3.16 |
| Mol. isobutene consumed/Mol. butene | — | 1.29 | 1.30 | — | 1.13 | 1.11 | — | 1.11 | 1.09 |
| % butene alkylated* | — | 100 | 100 | — | 100 | 100 | — | 100 | 100 |
| F-1 Octane No. | — | 79.6 | 76.7 | — | 81.5 | 83.5 | — | 84.1 | 88.0 |

*estimated

What is claimed is:

1. A process for alkylating an isoparaffinic hydrocarbon with an olefinic hydrocarbon which comprises contacting a mixture of said isoparaffinic hydrocarbon and said olefinic hydrocarbon, at alkylation conditions including a temperature of about −80°F to 150°F, with a catalytic composition comprising hydrogen fluoride-antimony pentafluoride on a fluorided alumina support, said support having a fluorine content of at least about 60 weight percent and a pore volume of about 0.05 cc to about 0.7 cc per gram.

2. A process in accordance with claim 1 wherein said alkylatable hydrocarbon is a $C_4$-$C_6$ isoparaffin and said olefin is a $C_2$-$C_6$ olefin.

3. A process in accordance with claim 1 wherein said catalytic composite has a surface area between 0.1 and 10 m²/gram.

* * * * *